US009479913B2

(12) United States Patent
Uchida (10) Patent No.: US 9,479,913 B2
(45) Date of Patent: Oct. 25, 2016

(54) MOBILE COMMUNICATION DEVICE AND COMMUNICATION METHOD

(75) Inventor: Kaoru Uchida, Kanagawa (JP)

(73) Assignee: NEC CORPORATION, Tokyo (JP)

( * ) Notice: Subject to any disclaimer, the term of this patent is extended or adjusted under 35 U.S.C. 154(b) by 167 days.

(21) Appl. No.: 13/977,436

(22) PCT Filed: Oct. 31, 2011

(86) PCT No.: PCT/JP2011/006082
§ 371 (c)(1),
(2), (4) Date: Jun. 28, 2013

(87) PCT Pub. No.: WO2012/098601
PCT Pub. Date: Jul. 26, 2012

(65) Prior Publication Data
US 2013/0300578 A1    Nov. 14, 2013

(30) Foreign Application Priority Data
Jan. 19, 2011   (JP) .................. 2011-008558

(51) Int. Cl.
*G08C 19/22*  (2006.01)
*H04Q 9/00*   (2006.01)
(Continued)

(52) U.S. Cl.
CPC .............. *H04W 4/20* (2013.01); *A61B 5/0022* (2013.01); *A61B 5/6801* (2013.01);
(Continued)

(58) Field of Classification Search
USPC .................. 340/870.01–870.44, 500–693.12, 340/3.1–16.1
See application file for complete search history.

(56) References Cited

U.S. PATENT DOCUMENTS

2005/0085257 A1* 4/2005 Laird ................ A61B 5/04
455/550.1

2007/0058634 A1* 3/2007 Gupta ................ H04L 67/12
370/392
2008/0275309 A1* 11/2008 Stivoric ............... A61B 5/411
600/300

FOREIGN PATENT DOCUMENTS

CN         2575524 Y      9/2003
CN       101520815 A      9/2009
(Continued)

OTHER PUBLICATIONS

Communication dated Dec. 8, 2014 from the State Intellectual Property Office P.R. China in counterpart application No. 201180065507.X.

(Continued)

*Primary Examiner* — Firmin Backer
*Assistant Examiner* — Jerold Murphy
(74) *Attorney, Agent, or Firm* — Sughrue Mion, PLLC (57) ABSTRACT

A mobile communication device (10) that relays communication between a sensor device (50) located in a neighbor area and a server device (70) includes a biometric information receiving unit (20) that receives biometric information of a user wearing the sensor device (50) from the sensor device (50), a sensor unit (30) that detects a change of state in the mobile communication device (10), and a public network communication unit (40) that transmits the biometric information and information about the change of state to the server device (70) via a public network (60) and receives health management information generated in the server device (70) using the transmitted information. The biometric information receiving unit (20) transmits the health management information to the sensor device (50) for display on the sensor device (50).

10 Claims, 5 Drawing Sheets

(51) Int. Cl.
| | |
|---|---|
| *G08B 23/00* | (2006.01) |
| *G08C 15/06* | (2006.01) |
| *H04L 17/02* | (2006.01) |
| *H04M 3/00* | (2006.01) |
| *H04W 4/20* | (2009.01) |
| *A61B 5/00* | (2006.01) |
| *G06F 19/00* | (2011.01) |
| *H04L 12/28* | (2006.01) |
| *H04M 1/725* | (2006.01) |
| *H04W 4/00* | (2009.01) |
| *H04W 84/20* | (2009.01) |
| *H04L 29/08* | (2006.01) |
| *H04W 4/04* | (2009.01) |
| *H04W 88/04* | (2009.01) |

(52) U.S. Cl.
CPC ...... *G06F 19/3418* (2013.01); *H04L 12/2825* (2013.01); *G06F 19/345* (2013.01); *H04L 67/12* (2013.01); *H04M 1/72522* (2013.01); *H04W 4/005* (2013.01); *H04W 4/04* (2013.01); *H04W 84/20* (2013.01); *H04W 88/04* (2013.01)

(56) References Cited

FOREIGN PATENT DOCUMENTS

| | | |
|---|---|---|
| JP | 10-305016 A | 11/1998 |
| JP | 2002-368907 A | 12/2002 |
| JP | 2003-198759 A | 7/2003 |
| JP | 2003-310561 A | 11/2003 |
| JP | 2005-087731 A | 4/2005 |
| JP | 2006-263002 A | 10/2006 |
| JP | 2007-156909 A | 6/2007 |

OTHER PUBLICATIONS

International Search Report for PCT/JP2011/006082 dated Dec. 6, 2011.

Communication dated Aug. 27, 2015 from the State Intellectual Property Office of the People's Republic of China in counterpart application No. 201180065507.X.

* cited by examiner

| DEVICE ID | SENSOR ID | TIME STAMP | SENSOR DATA 1 | SENSOR DATA 2 |
|---|---|---|---|---|

MOBILE COMMUNICATION DEVICE AND COMMUNICATION METHOD

CROSS-REFERENCE TO RELATED APPLICATION

This is a National Stage Entry of Application No. PCT/JP2011/006082 filed Oct. 31, 2011, claiming priority based on Japanese Patent Application No. 2011-008558 filed Jan. 19, 2011, the contents of all of which are incorporated herein by reference in their entirety.

TECHNICAL FIELD

The present invention relates to a mobile communication device and a communication method and, particularly, to a mobile communication device that relays communication between a sensor device and a server device, and a communication method of the mobile communication device.

BACKGROUND ART

A service that, by incorporating a sensor device, communication functions and the like into electrical household appliances, analyzes sensor data detected by a sensor device in a server device and provides useful information for a user has been provided in recent years. For example, a sensor device that detects information related to a user's health such as a pulse meter, a pedometer, a thermometer or the like is mounted in a wrist watch which a user wears at all times, and a server device analyzes information detected by the sensor device and offers information providing services such as health check-up and better health advice.

Patent Literature 1 discloses a technique that transmits a blood glucose level measured using a small blood glucose measure to a server device or the like through a mobile phone. Specifically, a transfer device that converts blood glucose data measured using a small blood glucose measure into a format that can be transmitted from a mobile phone terminal to a server device or the like is used. The transfer device is used with a connector between the small blood glucose measure and the mobile phone.

Further, Patent Literature 2 discloses a configuration of a network in which a PHS terminal receives biometric data such as a brain wave detected in earphones by near field radio communication and transmits the received biometric data to a server connected to the network.

Further, Patent Literature 3 discloses a configuration of a network in which data detected by a health condition sensor that detects the health condition of a user is transmitted to a monitoring device through a mobile terminal device. The monitoring device receives position information of the mobile terminal device at the same time. Therefore, when the health condition of a user gets worse, a person who monitors the user using the monitoring device can contact an appropriate medical institution based on the position information of the mobile terminal device.

CITATION LIST

Patent Literature

PTL1: Japanese Unexamined Patent Application Publication No. 2002-368907
PTL2: Japanese Unexamined Patent Application Publication No. 2003-310561
PTL3: Japanese Unexamined Patent Application Publication No. 2003-198759

SUMMARY OF INVENTION

Technical Problem

However, the above-described Patent Literature 1 needs to connect the dedicated transfer device between a small blood glucose measure and a mobile phone and thus has a problem that a user feels inconvenience when transmitting blood glucose data. In Patent Literature 2, the device configuration is simplified compared to that of Patent Literature 1 because biometric data is transmitted to a PHS terminal by near field radio communication. However, in Patent Literature 2, biometric data is detected using earphones. Because the earphones are placed in the head and their use is limited to listening to music or the like, it is not possible to detect various sensor data. Accordingly, a server needs to make analysis using limited sensor data, and therefore useful information for a user cannot be obtained in some cases. Further, in Patent Literature 3, although the monitoring device receives the data detected by the health condition sensor and the position information of the mobile terminal device, the position information is used only to check the position of the mobile terminal device, and therefore useful information for a user cannot be notified in some cases as in Patent Literature 2.

To solve the above problems, an exemplary object of the invention is to provide a mobile communication device and a communication method that can generate information more useful for a user who provides sensor data and transmit the information to the user.

Solution to Problem

A mobile communication device according to a first exemplary aspect of the invention is a mobile communication device that relays communication between a sensor device located in a neighbor area and a server device connected to a public network, including a biometric information receiving unit for receiving biometric information of a user wearing the sensor device from the sensor device, a sensor unit built in the mobile communication device, for detecting a change of state in the mobile communication device, and a public network communication unit for transmitting the biometric information and information about the change of state in the mobile communication device to the server device via the public network, and receiving health management information generated in the server device using the biometric information and the information about the change of state in the mobile communication device, wherein the biometric information receiving unit transmits the health management information received by the public network communication unit to the sensor device so that the health management information is displayed on the sensor device.

A communication method according to a second exemplary aspect of the invention is a communication method in a mobile communication device that relays communication between a sensor device located in a neighbor area and a server device connected to a public network, the method including receiving biometric information of a user wearing the sensor device from the sensor device, detecting a change of state in the mobile communication device, built in the mobile communication device, transmitting the biometric information and information about the change of state in the mobile communication device to the server device via the public network, receiving health management information generated in the server device using the biometric information and the information about the change of state in the mobile communication device, and transmitting the health management information received by the public network communication unit to the sensor device so that the health management information is displayed on the sensor device.

A sensor device according to a third exemplary aspect of the invention is a sensor device located in a neighbor area of a mobile communication device, including a sensor unit for detecting biometric information of a user wearing the sensor device, a communication unit for transmitting the biometric information to the mobile communication device, and receiving health management information generated using the biometric information and information about a change of state in the mobile communication device, and a display unit for displaying the health management information.

A sensor network system according to a fourth exemplary aspect of the invention is a sensor network system including a sensor device located in a neighbor area, a server device connected to a public network, and a mobile communication device that relays communication between the sensor device and the public network, wherein the sensor device detects biometric information of a user wearing the sensor device, and transmits the biometric information to the mobile communication device, the mobile communication device detects a change of state in the mobile communication device, and transmits the biometric information and information about the change of state in the mobile communication device to the server device via the public network, and the server device generates health management information using the biometric information and the information about the change of state in the mobile communication device, and transmits the health management information to the sensor device through the mobile communication device so that the health management information is displayed on the sensor device.

Advantageous Effects of Invention

According to the invention, it is possible to provide a mobile communication device and a communication method that can generate information more useful for a user who provides sensor data and transmit the information to the user.

DESCRIPTION OF EMBODIMENTS (First Exemplary Embodiment)

Exemplary embodiments of the present invention are described hereinafter with reference to the drawings. A configuration example of a mobile communication device according to a first exemplary embodiment is described with reference to FIG. 1. A mobile communication device 10 includes a biometric information receiving unit 20, a sensor unit 30, and a public network communication unit 40. The mobile communication device 10 communicates with sensor devices 50 by radio communication. Further, the mobile communication device 10 communicates with a server device 70 via a public network 60. The server device 70 is connected to the public network 60.

Figure 1:
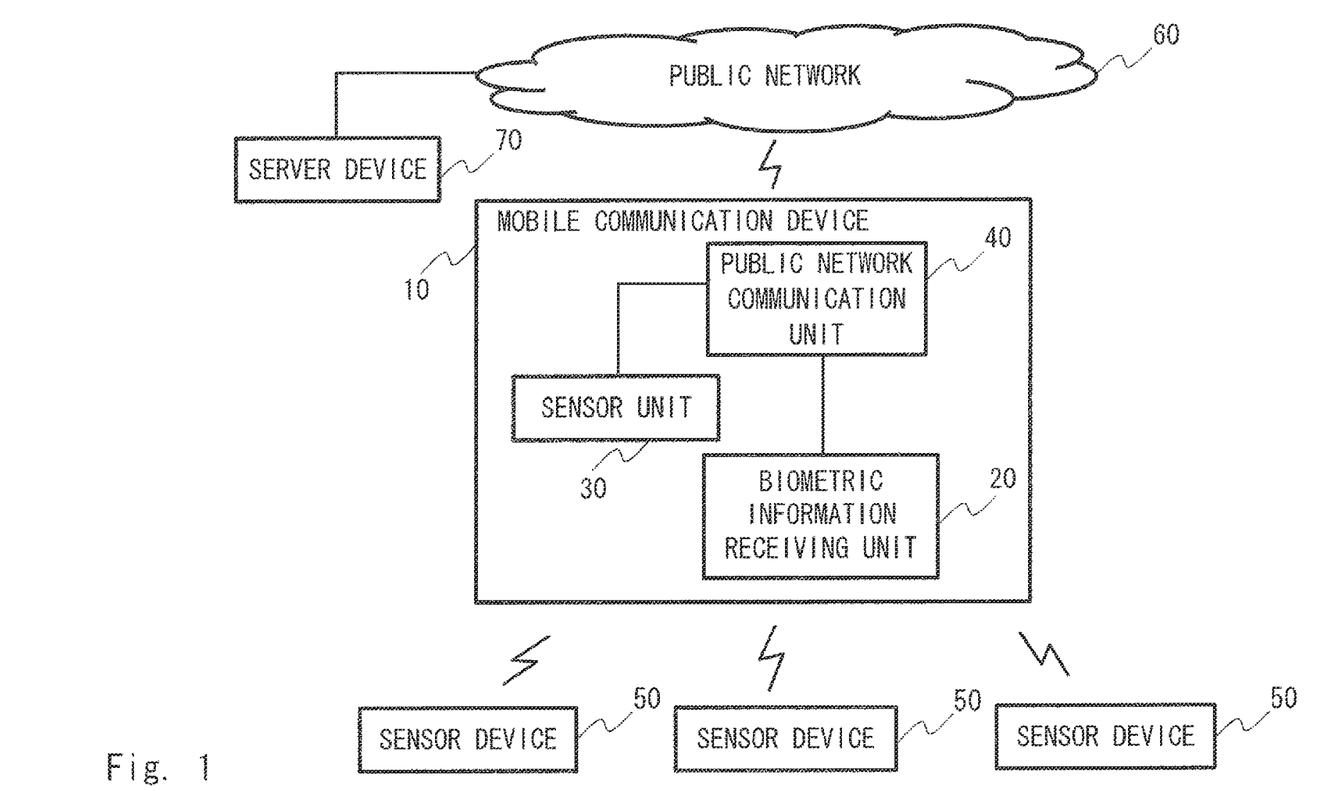
FIG. 1 is a block diagram of a mobile communication device according to a first exemplary embodiment.

The mobile communication device 10 relays communication between the sensor devices 50 located in the neighbor area of the mobile communication device 10 and the server device 70 connected to the public network 60. The mobile communication device 10 is a mobile phone terminal or a smartphone terminal, for example, which is a device with a communication function and easily portable.

The biometric information receiving unit 20 communicates with the sensor device 50 by radio and receives biometric information of a user who wears the sensor device 50. The biometric information is the body temperature, pulse rate, heart rate, steps and the like of a person who is wearing the sensor device 50, for example, which can be detected using a thermometer, pulse meter, pedometer and the like. The sensor device 50 is a thermometer, pulse meter, pedometer and the like, for example, and it may be a combination of a plurality of measuring instruments. Further, the sensor device 50 may be equipment incorporating a thermometer or the like, and it may be a wrist watch incorporating a thermometer, for example. The sensor device 50 has a communication function for radio communication.

The sensor unit 30 is built in the mobile communication device 10 and detects a change of state of the mobile communication device 10. For example, the sensor unit 30 is a GPS device and can receive latitude and longitude information where a mobile phone terminal 11 is located through a GPS antenna (not shown). Further, the sensor unit 30 may be an acceleration sensor, a temperature sensor or the like, and the mobile communication device 10 may include a plurality of sensors. The change of state occurs when a user of the mobile communication device 10 makes a move. For example, the change of state is a change in position or a change in moving speed when a user of the mobile communication device 10 has moved. Further, the change of state may be a change in step information of a user or a change in transportation such as walk or car on the basis of a change in moving speed.

The public network communication unit 40 transmits the biometric information received by the biometric information receiving unit 20 and information about the change of state in the mobile communication device 10 detected by the sensor unit 30 to the server device 70 via the public network 60. The server device 70 generates health management information using the biometric information and the information about the change of state in the mobile communication device 10.

The health management information is advice information for a user to live healthy. For example, the server device 70 receives step data detected by the sensor device 50 and geodetic history information with time stamps from the sensor unit 30 built in the mobile communication device 10. In this case, the sensor unit 30 is a positioning sensor having a GPS function. The server device 70 calculates the reliable amount of exercise from the step data and the geodetic history information with time stamps. Because the server device 70 can obtain an accurate moving distance not only from the step data but also using the geodetic history information, it is possible to calculate the reliable amount of exercise using the step data and the moving distance. Further, the server device 70 generates health management information such as "Walk at least B steps for A minutes" as a guide for the amount of exercise for the following day, for example, from the calculated amount of exercise.

After the mobile communication device 10 receives the health management information through the public network communication unit 40, the biometric information receiving unit 20 transmits the health management information to the sensor device 50 so that the health management information is displayed on the sensor device 50. A user wearing the sensor device 50 can thereby check the health management information displayed on a display unit (not shown) of the sensor device 50.

As described above, with use of the mobile communication device 10 shown in FIG. 1, the server device 70 can generate the health management information using the biometric information of a user detected by the sensor device 50 and the sensor data detected by the sensor unit 30 built in the mobile communication device 10. In this case, the biometric information of a user detected by the sensor device 50 can be corrected using the sensor data detected by the sensor unit 30 built in the mobile communication device 10, so that accurate health management information can be generated.

Figure 2:
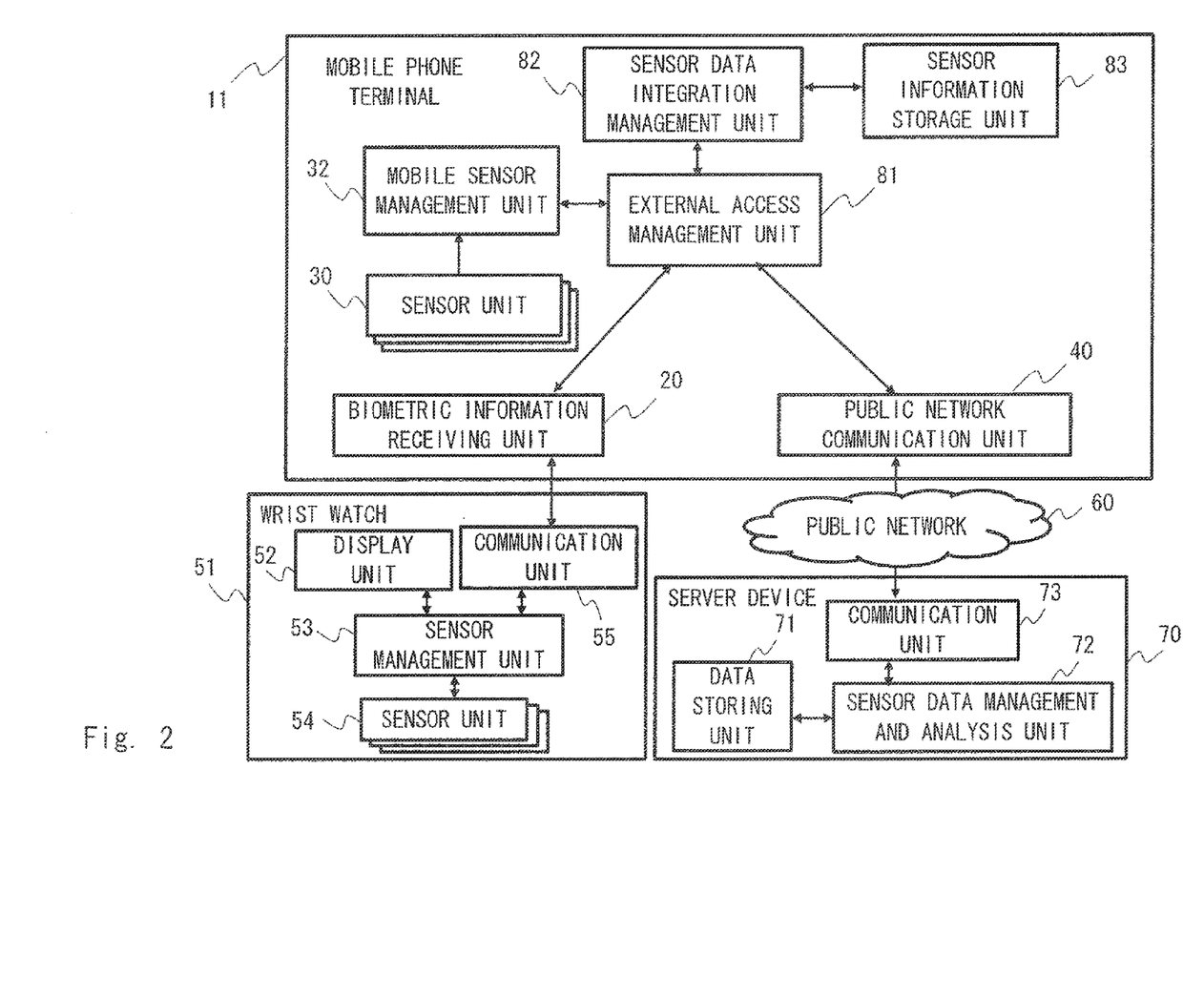
FIG. 2 is a block diagram of a mobile phone terminal, a sensor device and a server device according to the first exemplary embodiment.

Configuration examples of a mobile phone terminal 11, a wrist watch 51, and the server device 70 according to the first exemplary embodiment of the invention are described hereinafter with reference to FIG. 2. In FIG. 2, the mobile phone terminal 11 is used as a specific example of the mobile communication device 10. Further, the wrist watch 51 is used as a specific example of the sensor device 50.

The mobile phone terminal 11 includes a biometric information receiving unit 20, a sensor unit 30, a mobile sensor management unit 32, a public network communication unit 40, an external access management unit 81, a sensor data integration management unit 82, and a sensor information storage unit 83.

The public network communication unit 40 is the same as that of the mobile communication device 10 shown in FIG. 1 and not described in detail.

The biometric information receiving unit 20 performs near field radio communication with the sensor device 50 and receives the biometric information of a user wearing the sensor device 50. The near field radio communication is communication using infrared ray or communication using Bluetooth (registered trademark), Bluetooth Low Energy or the like, for example. Alternatively, the near field radio communication may be wireless LAN communication such as WiFi. In the case of using infrared ray, communication can be made with communication equipment at a distance of several tens of centimeters. In the case of using Bluetooth, communication can be made with communication equipment at a distance of several tens of meters. The neighbor area of the mobile communication device 10 is a range where near field radio communication is available.

The sensor unit 30 is a GPS device that detects the position information of the mobile phone terminal 11, an acceleration sensor, a temperature sensor or the like. The mobile phone terminal 11 may include one sensor or a plurality of sensors.

The mobile sensor management unit 32 receives sensor data detected by the sensor unit 30 and outputs it to the external access management unit 81. Further, the mobile sensor management unit 32 may temporarily store sensor data detected by the sensor unit 30 and, after a plurality of sensor data are accumulated, output the plurality of sensor data together to the external access management unit 81.

The external access management unit 81 has a Web server function (which is referred to hereinafter as a terminal server) and determines whether to allow connection to the server device 70 that makes an access through the public network communication unit 40, the wrist watch 51 that makes an access through the biometric information receiving unit 20 and the like. For example, an identifier of connectable equipment may be registered in the external access management unit 81 in advance. The server device 70, the wrist watch 51 and the like specify the URL and port number that are assigned to the terminal server and make an access to the mobile phone terminal 11. Further, the external access management unit 81 outputs sensor data transmitted from the wrist watch 51 and sensor data detected by the sensor unit 30 built in the mobile phone terminal 11 to the sensor data integration management unit 82. For example, the wrist watch 51 may transmit an http message "transmit data" to the terminal server and thereby API "transfer sensor data in the past 24 hours" may be executed.

The sensor data integration management unit 82 integrates the received sensor data. Specifically, the sensor data integration management unit 82 associates the sensor data detected by the wrist watch 51 and the sensor data obtained by the sensor unit 30 with each other and stores them as integrated data into the sensor information storage unit 83. For example, when the pulse data of a user is detected in the wrist watch 51 and the acceleration of the mobile phone terminal 11 is detected in the sensor unit 30, the sensor data integration management unit 82 stores the pulse data and the acceleration in association with each other into the sensor information storage unit 83. In this case, time stamp data when the pulse data and the acceleration are detected may be also recorded, and the data whose time stamps coincide or difference in time stamp is within a specified range may be associated with each other.

The external access management unit 81 transmits the integrated data integrated by the sensor data integration management unit 82 and stored in the sensor information storage unit 83 to the server device 70 through the public network communication unit 40. Further, the external access management unit 81 receives health management information generated using the integrated data from the server device 70. The external access management unit 81 then transmits the received health management information to the wrist watch 51 through the biometric information receiving unit 20.

A configuration example of the wrist watch 51 is described next. The wrist watch 51 includes a display unit 52, a sensor management unit 53, a sensor unit 54, and a communication unit 55. The sensor unit 54 detects information about a change of state in the wrist watch 51. For example, when the sensor unit 54 has a thermometer function, it detects the body temperature of a user wearing the wrist watch 51. Further, the sensor unit 54 may have a pulse meter function or the like as described above. Sensor data detected by the sensor unit 54 is output to the sensor management unit 53.

The sensor management unit 53 outputs the sensor data received from the sensor unit 54 to the communication unit 55 and transmits the sensor data to the mobile phone terminal 11 through the communication unit 55. The sensor management unit 53 may store the sensor data and transmit the stored sensor data to the mobile phone terminal 11 at predetermined timing. For example, the sensor data may be transmitted to the mobile phone terminal 11 when a user takes off the wrist watch at night after one day activity. Further, the sensor management unit 53 receives health management information output through the communication unit 55. The sensor management unit 53 outputs the received health management information to the display unit 52. The received health management information is then displayed on the display unit 52, and thereby a user can check the health management information displayed on the display unit 52.

Figure 3:
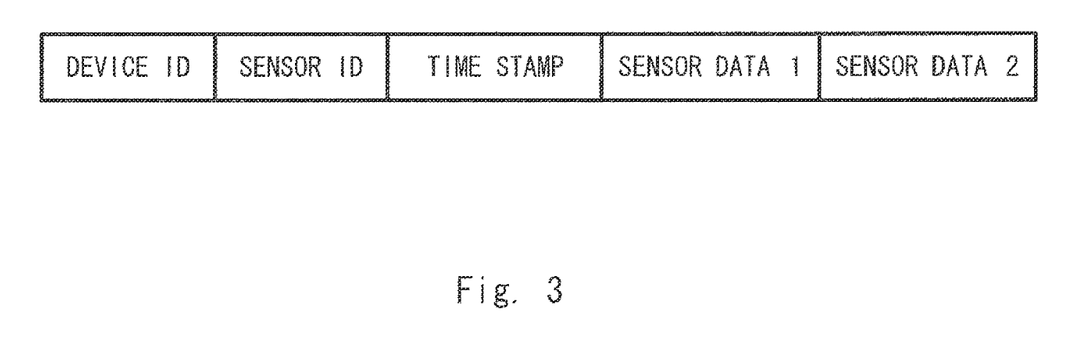
FIG. 3 is a diagram showing a data format of a frame used for transmission of sensor data according to the first exemplary embodiment.

A data format of a frame that is used for transmission of sensor data transmitted from the communication unit 55 to the mobile phone terminal 11 is described with reference to FIG. 3. The sensor data includes a device ID, a sensor ID, a time stamp and sensor data, for example. The device ID is ID for identifying the sensor device 50, and it is ID for identifying the wrist watch 51, for example. The sensor ID is ID for identifying the sensor built in the sensor device 50. The time stamp is time information when sensor data 1 and sensor data 2 are detected. The sensor data 1 and the sensor data 2 are data of body temperature information or the like when the sensor is a thermometer, for example.

A configuration example of the server device 70 is described hereinbelow. The server device 70 includes a data storing unit 71, a sensor data management and analysis unit 72, and a communication unit 73. The communication unit 73 communicates with the mobile phone terminal 11 via the public network 60. The communication unit 73 receives the integrated data from the mobile phone terminal 11. The communication unit 73 outputs the received integrated data to the sensor data management and analysis unit 72.

The sensor data management and analysis unit 72 analyzes the received integrated data and generates the health management information. An example of generation of the health management information is described hereinafter. The case where the pulse rate detected in the wrist watch 51 and the moving distance information detected in the sensor unit 30 are contained in the integrated data is described. The wrist watch 51 can detect the pulse rate by using a pulse meter in the sensor unit 54. Further, the mobile phone terminal 11 can detect the moving distance in a specified period by using a GPS device in the sensor unit 30. The sensor data management and analysis unit 72 receives the moving distance in a specified period and the transition of the pulse rate during the specified period as the integrated data. The sensor data management and analysis unit 72 analyzes the load, impact, effect and the like on the cardiopulmonary and circulatory system by the exercise performed during the specified period from the received integrated data.

As a result of analysis, the sensor data management and analysis unit 72 generates information about a suitable amount of exercise as health management information and transmits the health management information to the mobile phone terminal 11 through the communication unit 73. Further, the information generated in the sensor data management and analysis unit 72 is stored into the data storing unit 71. The information about a suitable amount of exercise is "Jog at the speed of about C km/h to raise the pulse rate from A to B over a specified period" or the like, for example, as described above.

The analysis of the integrated data in the sensor data management and analysis unit 72 is described using a different example. For example, in the case where a blood pressure and a heart rate detected in the wrist watch 51 and step information and position information detected in the sensor unit 30, where the sensor unit 30 is an acceleration sensor and a GPS, are contained in the integrated data, the timing of drinking water is estimated from the information about the blood pressure and the heart rate and the step information. Further, it can be determined whether there is a vending machine, a store or the like nearby from the position information. From those information, the sensor data management and analysis unit 72 can generate "Time to drink water. Vending machine 50 meters ahead" or the like as the health management information.

As another example, in the case where a blood pressure and a heart rate detected in the wrist watch 51 and body fat information transmitted daily from a body fat monitor as another sensor device to the mobile phone terminal 11 and accumulated are contained in the integrated data, the sensor data management and analysis unit 72 can generate information about a suitable amount of exercise from the transition of the body fat.

Further, the sensor data management and analysis unit 72 may transmit the information about a suitable amount of exercise generated in the above manner to a treadmill or the like used by a user and thereby control the speed, exercise intensity and the like of the treadmill automatically.

Figure 4:
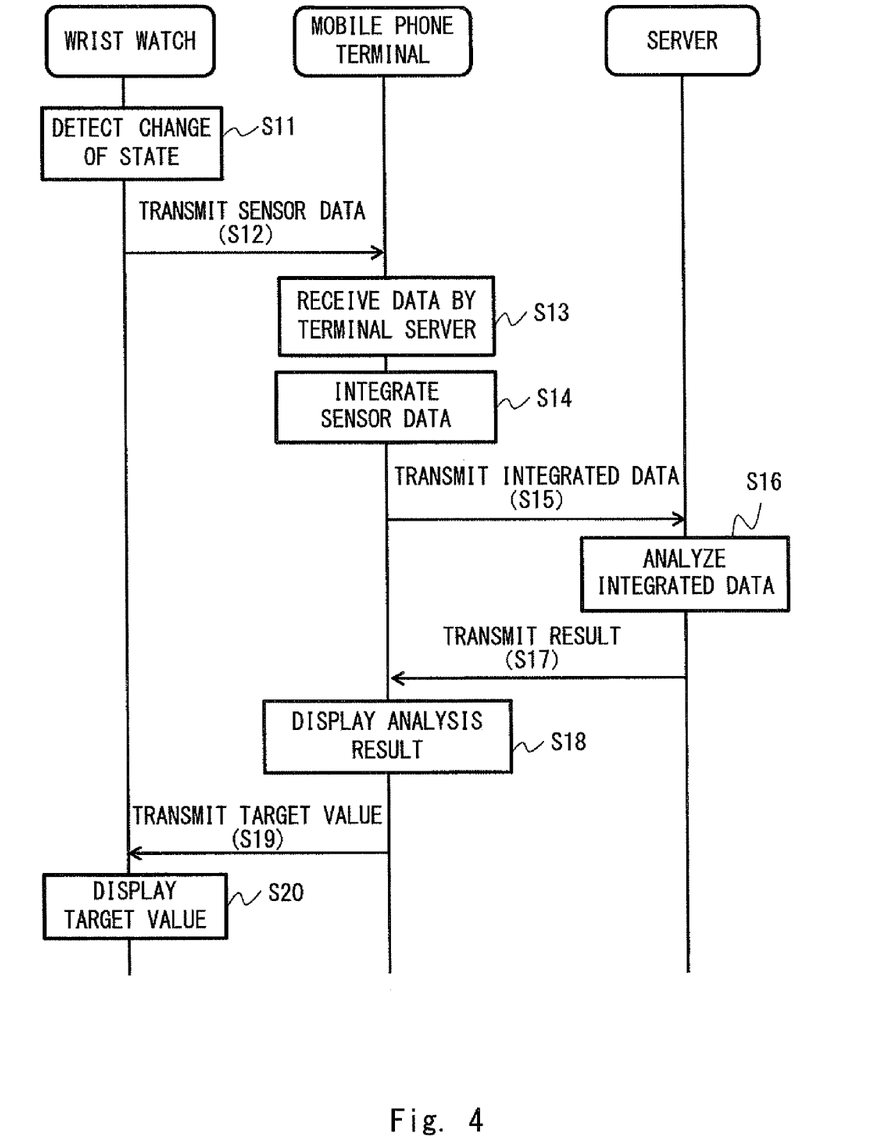
FIG. 4 is a flow of a process when receiving a health information providing service according to the first exemplary embodiment.

A flow of a process when receiving a health information providing service according to the first exemplary embodiment of the invention is described hereinafter with reference to FIG. 4. First, the sensor unit 54 of the wrist watch 51 detects a change of state by its sensor function (S11). Next, the communication unit 55 transmits sensor data detected by the sensor unit 54 to the mobile phone terminal 11 by near field radio communication (S12). The mobile phone terminal 11 receives the sensor data by the terminal server in the external access management unit 81 through the biometric information receiving unit 20 (S13). Then, the sensor data integration management unit 82 integrates, or associates, the sensor data received from the wrist watch 51 and the sensor data detected in the sensor unit 30 with each other and stores the integrated data into the sensor information storage unit 83 (S14). Further, the sensor data integration management unit 82 outputs the integrated data to the external access management unit 81. The external access management unit 81 transmits the integrated data to the server device 70 through the public network communication unit 40 (S15). The sensor data management and analysis unit 72 of the server device 70 analyzes the received integrated data and generates health management information (S16).

After that, the sensor data management and analysis unit 72 transmits the health management information to the mobile phone terminal 11 through the communication unit 73 (S17). The health management information is information about a suitable amount of exercise, such as "Jog at the speed of about C km/h to raise the pulse rate from A to B over a specified period", for example. Then, the external access management unit 81 of the mobile phone terminal 11 displays the received health management information on a display unit (not shown) (S18). The external access management unit 81 then transmits the health management information to the wrist watch 51 as a target value to keep good health (S19). The sensor management unit 53 of the wrist watch 51 displays the received health management information on the display unit 52 (S20). A user wearing the wrist watch can thereby check the health management information.

As described above, by using the mobile phone terminal 11 according to the first exemplary embodiment of the invention, the wrist watch 51 and the server device 70 can access the URL set to the terminal server in the mobile phone terminal 11. Thus, the mobile phone terminal 11 can relay communication between the wrist watch 51 and the server device 70. Further, the mobile phone terminal 11 can transmit the sensor data detected in the wrist watch 51 and the sensor data detected in the sensor built in the mobile phone terminal 11 to the server device 70. The server device 70 can thereby generate the health management information using those sensor data, and therefore it is possible to provide effective health management information compared to the case of using the sensor data detected in the wrist watch 51 only.

Further, compared to the case where the mobile phone terminal 11 operates with an application created specially for communicating with the wrist watch 51 and the server, transmitting and receiving data, and displaying and accumulating data and the like, the present invention that uses the terminal server has the following advantages. In the case where the terminal server receives data transmitted from the wrist watch 51 and communicates with the server device 70, processing such as transmitting the data received from the wrist watch 51 and the data detected by the sensor built in the mobile phone terminal 11 in synchronization with each other to the server device 70 and transmitting the health management information received from the server device 70 to the wrist watch 51 does not require explicit involvement by a user such as a user's operation on the mobile phone terminal 11. Thus, the processing is executed automatically on the background behind the operation of the mobile phone terminal 11 without any special user operation. Users are thereby free from an inconvenience of operation, and there is thus an advantage that users can easily manage their health on a daily basis.

Further, although the wrist watch 51 is used as an example of the sensor device 50 in the above description, a variety of equipment may be used as the sensor device 50 as long as it can execute Web API of the external access management unit 81 using an HTTP message.

For example, measured data of a user may be transmitted from home health instruments such as a blood-pressure meter, a body fat monitor and a body composition meter to the mobile phone terminal 11 and used for generation of the health management information. Further, consumed calories when playing a virtual game or the like may be transmitted to the mobile phone terminal 11. Furthermore, exercise record data, heart rate measurement result and the like from an exercise machine such as an exercise bike in an athletic gym may be transmitted to the mobile phone terminal 11.

(Second Exemplary Embodiment)

Figure 5:
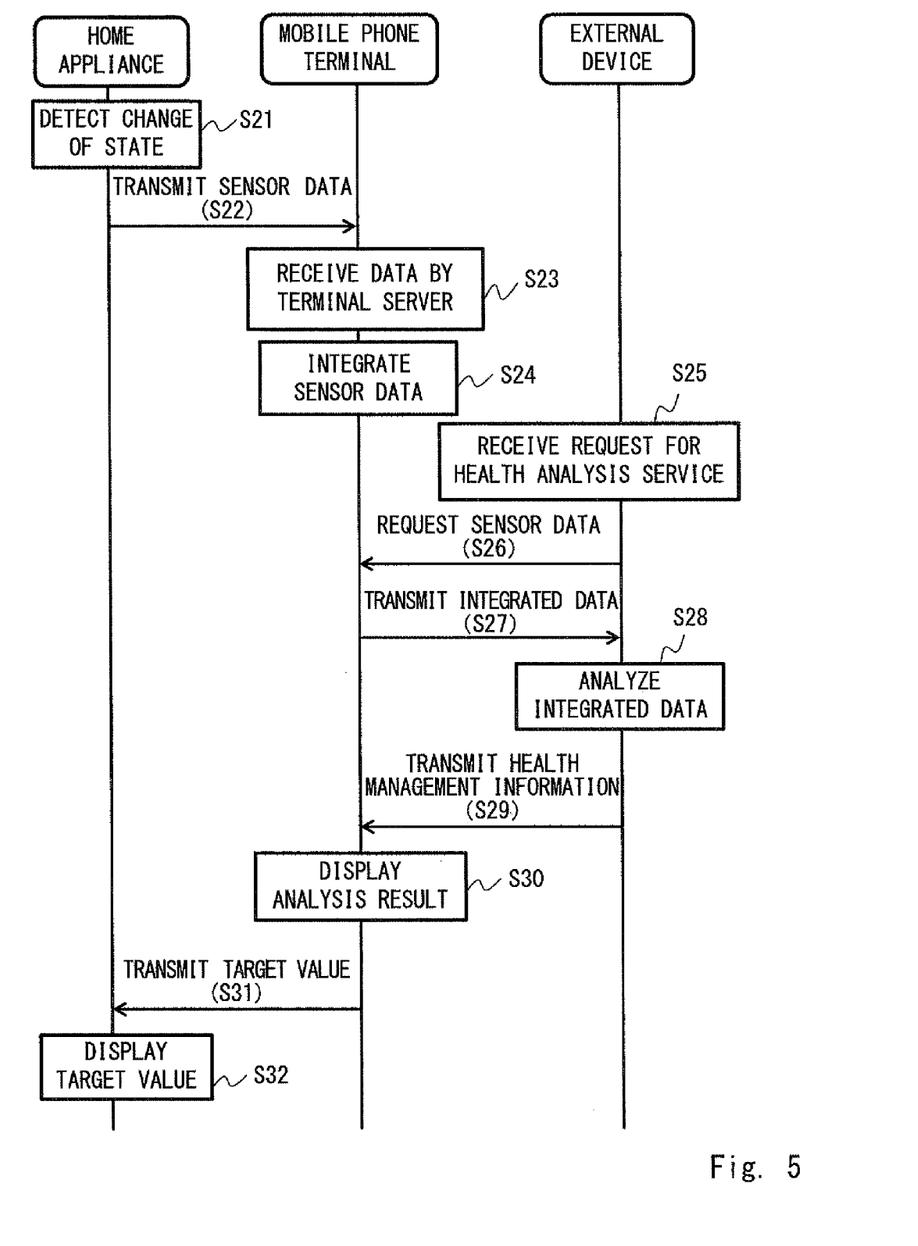
FIG. 5 is a flow of a process when receiving a health information providing service according to a second exemplary embodiment.

A flow of a process when receiving a health information providing service according to a second exemplary embodiment of the invention is described hereinafter with reference to FIG. 5. The processing of Steps S21 to S24 is the same as the processing of Steps S11 to S14 in FIG. 4 and not redundantly described.

After that, the server device 70 receives a request for execution of a health analysis service from a personal computer or the like (S25). The health analysis service is a service to receive advice for maintaining good health in a personal computer or the like.

Then, the server device 70 transmits a signal for requesting transmission of sensor data collected most recently to the terminal server in the mobile phone terminal 11 (S26). The sensor data integration management unit 82 of the mobile phone terminal 11 transmits the integrated data to the server device 70 through the public network communication unit 40 (S27). Steps S28 to S32 are the same as Steps S16 to S20 in FIG. 4 and not redundantly described.

As described above, by using the mobile phone terminal 11 according to the second exemplary embodiment of the invention, it is possible to respond to a request for transmitting sensor data which is made by the server device 70. This is because the mobile phone terminal 11 includes the terminal server and can thereby accept an access from the server device 70. Further, by creating Web contents in the terminal server of the mobile phone terminal 11 and making an access to the terminal server from a home personal computer or the like, it is possible to display and check the sensor data and the health management information.

The present invention is not restricted to the above-described exemplary embodiments, and various changes and modifications may be made without departing from the scope of the invention.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

This application is based upon and claims the benefit of priority from Japanese patent application No. 2011-008558, filed on Jan. 19, 2011, the disclosure of which is incorporated herein in its entirety by reference.

REFERENCE SIGNS LIST

10 MOBILE COMMUNICATION DEVICE
11 MOBILE PHONE TERMINAL
20 BIOMETRIC INFORMATION RECEIVING UNIT
30 SENSOR UNIT
32 MOBILE SENSOR MANAGEMENT UNIT
40 PUBLIC NETWORK COMMUNICATION UNIT
50 SENSOR DEVICE
51 WRIST WATCH
52 DISPLAY UNIT
53 SENSOR MANAGEMENT UNIT
54 SENSOR UNIT
55 COMMUNICATION UNIT
60 PUBLIC NETWORK
70 SERVER DEVICE
71 DATA STORING UNIT
72 SENSOR DATA MANAGEMENT AND ANALYSIS UNIT
73 COMMUNICATION UNIT
81 EXTERNAL ACCESS MANAGEMENT UNIT
82 SENSOR DATA INTEGRATION MANAGEMENT UNIT
83 SENSOR INFORMATION STORAGE UNIT

The invention claimed is:

1. A mobile communication device that relays communication between a sensor device located in a neighbor area and a server device connected to a public network, comprising:
   a biometric information receiving unit that receives biometric information of a user wearing the sensor device from the sensor device;
   a sensor unit built in the mobile communication device, that detects a change of state in the mobile communication device;
   a public network communication unit that transmits the biometric information and information about the change of state in the mobile communication device to the server device via the public network, and receives health management information generated in the server device using the biometric information and the information about the change of state in the mobile communication device; and
an access management unit that accepts an access using a hyper-text transfer protocol (http) message from the sensor device, and accepts an access using an http message from the server device through the public network communication unit,
wherein the biometric information receiving unit transmits the health management information received by the public network communication unit to the sensor device so that the health management information is displayed on the sensor device, and
the access management unit transmits the biometric information of the user and the information about the change of state in the mobile communication device to the server device through the public network communication unit based on an application programing interface (API) execution instruction transmitted from the sensor device.

2. The mobile communication device according to claim 1, wherein the biometric information receiving unit receives the biometric information from the sensor device and transmits the health management information generated in the server device to the sensor device by radio communication with the sensor device.

3. The mobile communication device claim 1, wherein the access management unit transmits the biometric information of the user and the information about the change of state in the mobile communication device to the server device through the public network communication unit based on an API execution instruction transmitted from the server device.

4. The mobile communication device according to claim 1, wherein the access management unit transmits the biometric information and the information about the change of state in the mobile communication device to the server device through the public network communication unit when a request for transmitting the biometric information and the information about the change of state in the mobile communication device is made from the server device.

5. The mobile communication device according to claim 1, wherein the access management unit manages the health management information received through the public network communication unit in association with a Web content viewable from external communication equipment that makes any of the access using the http message from the sensor device and the access using the http message from the server device.

6. A sensor network system comprising:
a sensor device located in a neighbor area;
a server device connected to a public network;
an access management device that accepts an access using a hyper-text transfer protocol (http) message from the sensor device, and accepts an access using an http message from the server device through a public network communication unit; and
a mobile communication device that relays communication between the sensor device and the public network, wherein
the sensor device detects biometric information of a user wearing the sensor device, and transmits the biometric information to the mobile communication device,
the mobile communication device detects a change of state in the mobile communication device, and transmits the biometric information and information about the change of state in the mobile communication device to the server device via the public network,
the server device generates health management information using the biometric information and the information about the change of state in the mobile communication device, and transmits the health management information to the sensor device through the mobile communication device so that the health management information is displayed on the sensor device, and
the access management device transmits the biometric information of the user and the information about the change of state in the mobile communication device to the server device through the public network based on an application programing interface (API) execution instruction transmitted from the sensor device.

7. A mobile communication device that relays communication between a sensor device located in a neighbor area and a server device connected to a public network, comprising:
biometric information receiving means for receiving biometric information of a user wearing the sensor device from the sensor device;
sensor means built in the mobile communication device, for detecting a change of state in the mobile communication device;
public network communication means for transmitting the biometric information and information about the change of state in the mobile communication device to the server device via the public network, and receives health management information generated in the server device using the biometric information and the information about the change of state in the mobile communication device; and
access management means that accept an access using a hyper-text transfer protocol (http) message from the sensor device, and accepts an access using an http message from the server device through the public network communication means,
wherein the biometric information receiving means transmits the health management information received by the public network communication means to the sensor device so that the health management information is displayed on the sensor device, and
wherein the access management means transmits the biometric information of the user and the information about the change of state in the mobile communication device to the server device through the public network communication unit based on an application programing interface (API) execution instruction transmitted from the sensor device.

8. A communication method in a mobile communication device that relays communication between a sensor device located in a neighbor area and a server device connected to a public network, the method comprising:
receiving, by the mobile communication device, biometric information of a user wearing the sensor device from the sensor device;
detecting, by the mobile communication device, a change of state in the mobile communication device;
transmitting, by the mobile communication device, the biometric information and information about the change of state in the mobile communication device to the server device via the public network;
receiving, by the mobile communication device, health management information generated in the server device using the biometric information and the information about the change of state in the mobile communication device;

transmitting, by the mobile communication device, the received health management information to the sensor device so that the health management information is displayed on the sensor device;

accepting, by the mobile communication device, an access using a hyper-text transfer protocol (http) message from the sensor device when receiving biometric information of a user; and accepting, by the mobile communication device, an access using an http message from the server device via the public network when receiving the health management information, wherein when transmitting the biometric information and the information about the change of state in the mobile communication device to the server device via the public network, the biometric information of the user and the information about the change of state in the mobile communication device are transmitted, by the mobile communication device, to the server device via the public network based on an application programming interface (API) execution instruction transmitted from the sensor device.

9. The communication method according to claim 8, wherein when transmitting the biometric information and the information about the change of state in the mobile communication device to the server device via the public network, the biometric information of a user and the information about the change of state in the mobile communication device are transmitted, by the mobile communication device, to the server device via the public network based on an API execution instruction transmitted from the server device.

10. The communication method according to claim 8, wherein the biometric information and the information about the change of state in the mobile communication device are transmitted, by the mobile communication device, to the server device via the public network when a request for transmitting the biometric information and the information about the change of state in the mobile communication device is made from the server device.

* * * * *